United States Patent
TenHuisen et al.

(10) Patent No.: US 6,958,158 B2
(45) Date of Patent: Oct. 25, 2005

(54) IMMUNE MODULATION DEVICE FOR USE IN ANIMALS

(75) Inventors: Kevor S. TenHuisen, Clinton, NJ (US); Joel Rosenblatt, Watchung, NJ (US); Ilya S. Koyfman, Ringoes, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 10/103,087

(22) Filed: Mar. 21, 2002

(65) Prior Publication Data

US 2003/0068812 A1 Apr. 10, 2003

Related U.S. Application Data

(60) Provisional application No. 60/290,542, filed on May 11, 2001.

(51) Int. Cl.[7] .............................. A61F 2/00; A61K 9/00; A61K 39/00; A61M 31/00

(52) U.S. Cl. ....................... 424/424; 424/423; 424/426; 424/184.1; 604/19; 604/93.01

(58) Field of Search .................................. 424/422, 423, 424/424, 425, 426, 443, 451, 457, 462, 93.1, 93.7, 93.21, 184.1; 435/5, 69.1, 69.7, 293.1, 297.1, 325, 345, 547, 548, 320.1; 436/547, 548; 442/123; 604/103.01, 890.1, 892.1, 43, 93.01, 19; 530/300, 350; 264/28, 126; 623/11.11

(56) References Cited

U.S. PATENT DOCUMENTS

| | | |
|---|---|---|
| 3,887,699 A | 6/1975 | Yolles |
| 4,052,550 A | 10/1977 | Chion et al. |
| 4,052,988 A | 10/1977 | Doddi et al. |
| 4,105,034 A | 8/1978 | Shalaby et al. |
| 4,128,612 A | * 12/1978 | Roth ........................ 264/126 |
| 4,130,639 A | 12/1978 | Shalaby et al. |
| 4,140,678 A | 2/1979 | Shalaby et al. |
| 4,141,087 A | 2/1979 | Shalaby et al. |
| 4,164,560 A | 8/1979 | Folkman et al. |
| 4,205,399 A | 6/1980 | Shalaby et al. |
| 4,208,511 A | 6/1980 | Shalaby et al. |
| 4,224,946 A | 9/1980 | Kaplan |
| 4,314,561 A | 2/1982 | Kaplan |
| 4,520,822 A | 6/1985 | Menezes et al. |
| 4,557,264 A | 12/1985 | Hinsch |
| 4,564,013 A | 1/1986 | Lilenfeld et al. |
| 4,605,730 A | 8/1986 | Shalaby et al. |
| 4,700,704 A | 10/1987 | Jamiolkowski et al. |
| 4,732,155 A | 3/1988 | Zetter et al. |
| 4,919,929 A | 4/1990 | Beck |
| 5,088,505 A | 2/1992 | De Nijs |
| 5,102,419 A | 4/1992 | Gertzman et al. |

(Continued)

FOREIGN PATENT DOCUMENTS

EP      0 287 899 A2    10/1988

(Continued)

OTHER PUBLICATIONS

U.S. Appl. No. 10/017,457, Cerami et al.
Vallera et al. (1982, Cancer Research 42:397–404.

(Continued)

Primary Examiner—James Housel
Assistant Examiner—Zachariah Lucas

(57) ABSTRACT

The present invention is directed to an implantable immune modulation device that is useful for modulating an immune response in mammals, comprising a plurality of fibers, within a porous shell. The fiber filling is loaded with single or multiple antigens, and optionally one or more biologically active compounds such as cytokines (e.g. lymphokines, chemokines etc.), attachment factors, genes, peptides, proteins, nucleotides, carbohydrates or cells depending on the application.

32 Claims, 3 Drawing Sheets

U.S. PATENT DOCUMENTS

| | | | |
|---|---|---|---|
| 5,133,739 A | 7/1992 | Bezwada et al. | |
| 5,147,382 A | 9/1992 | Gertzman et al. | |
| 5,269,807 A | 12/1993 | Liu | |
| 5,431,679 A | 7/1995 | Bennett et al. | |
| 5,442,032 A | 8/1995 | Arnold et al. | |
| 5,464,929 A | 11/1995 | Bezwada et al. | |
| 5,542,594 A | 8/1996 | McKean et al. | |
| 5,595,751 A | 1/1997 | Bezwada et al. | |
| 5,597,579 A | 1/1997 | Bezwada et al. | |
| 5,607,687 A | 3/1997 | Bezwada et al. | |
| 5,618,552 A | 4/1997 | Bezwada et al. | |
| 5,620,698 A | 4/1997 | Bezwada et al. | |
| 5,645,850 A | 7/1997 | Bezwada et al. | |
| 5,648,088 A | 7/1997 | Bezwada et al. | |
| 5,676,943 A * | 10/1997 | Baetge et al. | 424/93.21 |
| 5,698,213 A | 12/1997 | Jamiolkowski et al. | |
| 5,700,533 A | 12/1997 | You | |
| 5,703,200 A | 12/1997 | Bezwada et al. | |
| 5,725,854 A | 3/1998 | Selawry | |
| 5,795,584 A | 8/1998 | Totakura et al. | |
| 5,854,383 A | 12/1998 | Erneta et al. | |
| 5,859,150 A | 1/1999 | Jamiolkowski et al. | |
| 6,031,148 A * | 2/2000 | Hayes et al. | 623/11.11 |
| 6,045,560 A | 4/2000 | McKean et al. | |
| 6,200,589 B1 * | 3/2001 | Kennedy et al. | 424/424 |
| 6,303,136 B1 * | 10/2001 | Li et al. | 424/424 |
| 6,334,968 B1 * | 1/2002 | Shapiro et al. | 264/28 |
| 6,551,355 B1 * | 4/2003 | Lewandrowski et al. | 623/16.11 |
| 2003/0118630 A1 | 6/2003 | Cerami et al. | |

FOREIGN PATENT DOCUMENTS

| | | |
|---|---|---|
| EP | 0 300 102 A1 | 1/1989 |
| EP | 0 448 840 A2 | 10/1991 |
| WO | WO 85/03635 A1 | 8/1985 |
| WO | WO 91/19464 * | 12/1991 |
| WO | WO 93/17662 A1 | 9/1993 |
| WO | WO 99/44583 A2 | 9/1999 |

OTHER PUBLICATIONS

Zangemeister–Wittke et al. (1989, J. Immunol. 143:379–385).

Journal of Biomaterials Research, vol. 22, pp. 993–1009, 1988 by Cohn and Younes.

Artursson et al. "Biodegradable Microspheres II: Immune Response to a Heterologous and an Autologous Protein Entrapped in Polyacryl Starch Microparticles", The Journal of Pharmacology and Experimental Therapeutics, vol. 234, No. 1, pp. 255–260.

Ford–Hutchinson et al., "Assessment of Anti–inflammatory Activity By Sponge Implantation Techniques", 1978 Journal of Pharmacological Methods, vol. 1, pp. 3–7.

* cited by examiner x50 500μm

IMMUNE MODULATION DEVICE FOR USE IN ANIMALS

This application claims benefit of provisional patent application No. 60/290,542 filed May 11, 2001, which is hereby incorporated by reference herein.

FIELD OF THE INVENTION

The present invention relates to an implantable device and method for modulating the immune response to antigens in mammals. More specifically the present invention provides a porous, implantable device containing a fibrous support and at least one antigen. This device may be used to modulate the immune system to provide a robust response against an antigen, or to down regulate an existing response.

BACKGROUND OF THE INVENTION

Induction of an immune response to an antigen and the magnitude of that response depend upon a complex interplay among the antigen, various types of immune cells, and co-stimulatory molecules including cytokines. The timing and extent of exposure of the immune cells to the antigen and the co-stimulatory milieu further modulate the immune response. Within the body, these various cell types and additional factors are brought into proximity in lymphoid tissue such as lymph nodes. Of the numerous cell types involved in the process, antigen-presenting cells (APC), such as macrophages and dendritic cells, transport antigen from the periphery to local, organized lymphoid tissue, process the antigen and present antigenic peptides to T cells as well as secrete co-stimulatory molecules. Thus, if antigen reaches lymph organs in a localized staggered manner, presenting antigenic epitopes, under the optimal concentration gradient and under the appropriate environment comprising co-stimulatory molecules, a response is induced in the draining lymph node.

In this manner, a foreign antigen introduced into the body, such as by means of a vaccination, may or may not result in the development of a desirably robust immune response. Antigens used for vaccination include attenuated and inactivated bacteria and viruses and their components. The success of vaccination depends in part on the type and quantity of the antigen, the location of the site of immunization, and the status of the immune system at the time of vaccination. Not all antigens are equally immunogenic, and for poorly immunogenic antigens, there are few alternatives available to increase the effectiveness of the immunization. Whereas in experimental animals numerous techniques are available to enhance the development of the immune response, such as conjugating the antigen to a more immunogenic carrier protein or biomolecule (e.g., keyhole limpet hemocyanin), or the use of adjuvants such as Freund's Adjuvant or Ribi. For human vaccinations such techniques and adjuvants are not available. Thus, numerous diseases that would otherwise be preventable by vaccination before exposure to the infectious agent, or in the case of a therapeutic vaccine, that may induce the development of an effective immune response to an existing disease-causing agent or cell, such as cancer, are not available to the patient.

Sponge implant studies have been performed in mammals to assess the immune cell population attracted to a foreign body, which produce what is called a sterile abscess, and sponges prior to or after implantation have been loaded with antigen to further study the attracted cell population. Vallera et al. (1982, Cancer Research 42:397–404) implanted sponges containing tumor cells in mice to examine the composition of cells attracted over a 16 day period, and found that at an early time, cytotoxic cell precursors were present, and cytotoxicity peaked at day 16. Sponges containing tumor cells implanted in mice that had been previously immunized with tumor cells showed a more rapid appearance of cytotoxic cells in the sponge. In neither case did cells from the spleen, lymph nodes or peritoneum show cytotoxicity, which suggested a highly localized response to the antigen in the sponge. Zangemeister-Wittke et al. (1989, J. Immunol. 143:379–385) injected a tumor vaccine into sponges implanted in tumor-immune mice, and monitored the generation of a secondary immune response at the sponge site. No accompanying effect was apparent in lymph nodes adjacent to the implanted sponge.

Other devices which overcome some of the limitations of sponges for immunomodulation have been proposed. U.S. Pat. No. 4,919,929 teaches that an antigen can be loaded into solid shaped particles, which slowly release the antigen following implantation. This type of device is envisaged to increase the antibody titers in the milk of mammals and thereby confer higher levels of immunity in those who consume it. WO application 93/17662 describes a device that consists of an impervious membrane surrounding a core, which is a gel loaded with a therapeutically active ingredient (including antigens). There is at least one port in the impervious membrane that is capable of releasing the active to the surroundings. The use of the membrane is shown to slow the rate of release of the bioactive molecule (including antigens) relative to the gel alone. This device therefore primarily serves as a reservoir for slow release and does not facilitate the interaction of cells with the bioactive, which necessarily must occur outside of the device. In U.S. Pat. No. 4,732,155, a device is proposed where there is a reservoir that provides prolonged release of a chemoattractant, which is surrounded by a web of fibers adjacent to the reservoir. Cells are attracted to the reservoir and become trapped in the fibrous web. This device is proposed for use in characterizing allergic and inflammatory responses to test compounds by allowing controlled exposure to the compound and by trapping the cells that respond to it. This device both incorporates a mechanism for prolonged exposure to an antigen as well as a mechanism to facilitate cellular interaction with the antigen. The open web of fibers in this device; however, does not enable local retention of the cytokines and chemokines being secreted by the responding cells since an open web of fibers will not provide diffusional resistance to soluble factors.

This design is improved upon in WO 99/44583 which proposes a porous matrix which is housed in a perforated but otherwise impervious membrane. Antigen is loaded within the device and can be present either as native antigen or can be encapsulated in a slow releasing polymer that provides prolonged presentation of the antigen. Specific cells are attracted to the device by diffusion of the antigen from the perforations in the device and are also able to enter the device through the perforations, but the membrane provides sufficient diffusional resistance that cytokines secreted by cells become locally concentrated within the device. The high local densities of cells and cytokines produce a much more robust immune response than is seen with an uncontained matrix or with simple prolonged release to surrounding tissues.

The preferred embodiment of the device mentioned above envisages the porous matrix to be a sponge and the membrane to be a perforated tube. While very favorable immunomodulation is seen with the device, it is impractical to miniaturize and manufacture in large quantities. The primary reason is that it is very difficult to load a porous sponge into tubing. Sponges, due to their low bulk densities are mechanically weak and tend to tear easily when subjected to the tensile and compressive forces of loading into small diameter tubing. By reducing the bulk density, more favorable mechanical properties can be encountered however the matrix does not contain sufficient porosity to attain high cell densities. In addition, it is very difficult to cut small cylindrical cores of porous sponges for loading into tubes. The reason is that the poor mechanical properties of the porous sponge lead to tearing when the size of the piece being cut becomes very small. Consequently, the device envisaged in WO 99/44583 is only practical to make in diameters of greater than 1 mm. Implantation of such a large profile device requires a very sizable needle or trochar that would be very painful and cause significant local trauma to a patient. An additional problem with this device design is that it would be difficult to economically manufacture in large quantities. The reason is that each piece of sponge would need to be individually cut and stuffed into the tube. This would be very difficult to mechanize and perform rapidly.

Accordingly, it would be advantageous to provide an implantable device and method for modulating an immune response to specific antigens in mammals, similar in concept to the design described in WO 99/44583, whose filling preserves the porosity presented by a porous sponge, which is essential for rapid cellular infiltration, yet overcomes the mechanical frailties of a sponge.

SUMMARY OF THE INVENTION

The present invention is directed to an implantable immune modulation device that is suitable for use in modulating an immune response in mammals, comprising an impermeable shell having a plurality of pores and said impermeable biocompatible shell having an interior lumen, a biocompatible fibrous scaffolding being disposed within said interior lumen. The fibrous scaffolding is loaded with single or multiple antigens and optionally one or more biologically active compounds such as cytokines (e.g. lymphokines, chemokines etc.), non-cytokine leukocyte chemotactic agents, attachment factors, genes, peptides, proteins, nucleotides, carbohydrates, or cells depending on the application. The shell of the device preferably is made from a polymer whose glass transition temperature is below physiologic temperature so that the device will minimize irritation when implanted in soft tissues. The shell allows cell ingress but hinders diffusion of soluble molecules out of the device. This helps to concentrate cytokines (e.g. lymphokine and chemokines) secreted by cells which have entered the device in response to loaded antigens and other cells which are present in the device. This local concentration of cells and cytokines significantly enhances the immune response relative to implantation of antigens with standard adjuvants. The fibrous scaffolding provides a scaffold for cells to reside on, process the antigens and interact.

Additional benefits of the fibrous scaffolding disclosed in this invention include ease of miniaturization of a device to diameters of less than 1 mm, the possibility of rapid insertion into small diameter tubing or even the ability to have tubing continuously extruded around the matrix.

DETAILED DESCRIPTION OF THE INVENTION

Figure 1:
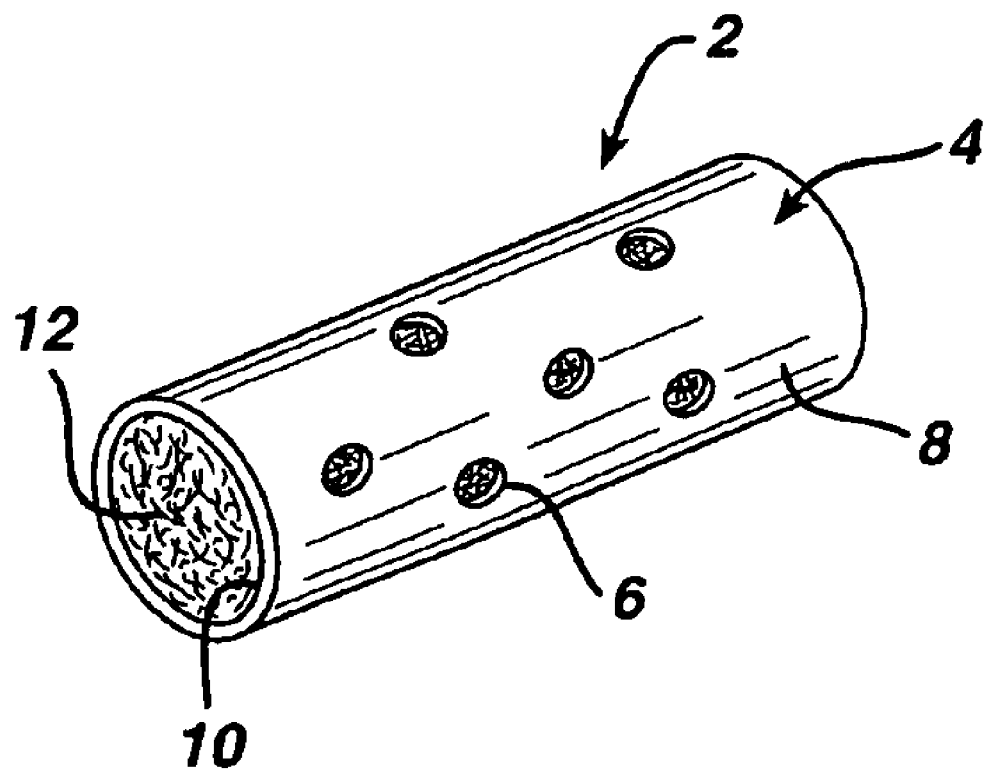
FIG. 1 is a perspective drawing of one embodiment of the immune modulating device described herein.

An immune modulation device is disclosed herein which allows for cell ingress and concentration of cytokines secreted by cells. A perspective view of the immune modulation device is provided in FIG. 1. The immune modulation device 2 is comprised of a shell 4 surrounding an interior lumen 10. The shell 4 has pores 6 that extend from the outer surface 8 to the interior lumen 10. The interior lumen will have a volume of at least $1 \times 10^{-8}$ cm$^3$, preferably will be at least $3 \times 10^{-8}$ cm$^3$ and most preferably the size of the lumen will be sufficient to elicit the desired immune response from the animal in which it is implanted (which can be determined by methods well known in the art such as ELISA). The shell 2 may have a variety of three dimensional shapes (e.g. cylindrical, spherical, rectangular, rhomboidal, etc.). For example the shell 2 will generally have a longitudinal axis and a cross-section that may be circular, oval or polygonal. Preferred for ease of manufacture is a cylindrical shape. A cylindrically shaped immune modulation device 2 is illustrated in FIG. 1. The ends of the cylindrically shaped immune modulation device may be capped or left open as illustrated in FIG. 1. The outer surface 8 of the immune modulation device 2 is preferably impervious to cytokines and immune cells and has numerous pores 6 that allow for the ingress and egress of immune cells. The number of pores 6 will generally be less than 25 percent of the outer surface and preferably will be less than about 10 percent of the outer surface. The pores 6 size may range from about 10 to about 500 microns and preferably in the range of from about 100 to about 400 microns. The interior 10 of immune modulation device 2 will be filled with a fibrous scaffolding 12 made of a plurality of fibers (e.g. a yarn or a tow).

The fibrous scaffolding 12 is made from biocompatible fibers, preferably textured fibers which provide a much lower bulk density filling than non-texturized fiber. The low bulk density of textured fibers enables rapid population of the immune modulation device 2 with significant numbers of cells and helps to retain the fibrous scaffolding 12 within the shell 4. The fibrous scaffolding 12 is loaded with single or, multiple antigens and optionally other biologically active or pharmaceutically active compounds (e.g. cytokines (e.g. interlukins 1–18; interferons $\alpha$, $\beta$, and $\gamma$; growth factors; colony stimulating factors, chemokines, tumor necrosis factor $\alpha$ and $\beta$, etc.), non-cytokine leukocyte chemotactic agents (e.g. C5a, LTB$_4$, etc.), attachment factors, genes, peptides, proteins, nucleotides, carbohydrates or synthetic molecules) or cells depending on the application.

The shell 4 and the fibrous scaffolding 12 of the device will be made with a biocompatible material that may be absorbable or non-absorbable. The device will preferably be made from biocompatible materials that are flexible and thereby minimizing irritation to the patient. Preferably the shell will be made from polymers or polymer blends having glass transition temperature below physiologic temperature. Alternatively the device can be made with a polymer blended with a plasticizer that makes it flexible.

In theory but in no way limiting the scope of this invention it is suspected that the shell allows cell ingress and egress but hinders diffusion of soluble molecules out of the device. This is believed to help to concentrate cytokines secreted by cells that have entered the device in response to loaded antigens (e.g. antigen presenting cells) and other cells (e.g. helper T cells, B cells etc.) which are present in the device. The fibrous scaffolding provides a scaffold for cells to reside on and process the antigens. This local concentration of cells and cytokines significantly enhances the immune response relative to implantation of antigens with standard adjuvants.

The intended recipient of the implantable device is an animal; preferably a human, but also including livestock animal, (e.g. sheep, cow, horse, pig, goat, lama, emu, ostrich or donkey), poultry (e.g. chicken, turkey, goose, duck, or game bird), fish (e.g. salmon or strugeon), laboratory animal (e.g. rabbit, guinea pig, rat or mouse) companion animal (e.g. dog or cat) or a wild animal in captive or free state.

Numerous biocompatible absorbable and nonabsorbable materials can be used to make the shell or fibrous scaffolding. Suitable nonabsorbable materials for use in as the shell or fibrous scaffolding include, but are not limited to, polyamides (e.g. polyhexamethylene adipamide (nylon 6,6), polyhexamethylene sebacamide (nylon 610), polycapramide (nylon 6), polydodecanamide (nylon 12) and polyhexamethylene isophthalamide (nylon 6I), copolymers and blends thereof), polyesters (e.g. polyethylene terephthalate, polybutyl terphthalate (e.g. as described in EPA 287,899 and EPA 448,840), copolymers (e.g. as described in U.S. Pat. No. 4,314,561; Re 32,770; U.S. Pat. Nos. 4,224,946; 5,102,419 and 5,147,382) and blends thereof), fluoropolymers (e.g. polytetrafluoroethylene and polyvinylidene fluoride copolymers (e.g. as described in U.S. Pat. No. 4,564,013) and blends thereof), polyolefins (e.g. polypropylene including atactic but preferably isotactic and syndiotactic polypropylene and blends thereof, as well as, blends composed predominately of isotactic or syndiotactic polypropylene blended with heterotactic polypropylene and polyethylene), organosiloxanes (e.g. polydimethylsiloxane rubber such as SILASTIC® silicone tubing from Dow Corning), polyvinyl resins (e.g. polystyrene, polyvinylpyrrolidone, etc.) and blends thereof.

Additionally the fibrous scaffolding may be made from natural fibers such as cotton, linen and silk (although silk is referred to as a nonabsorbable material, it is broken down in the human body). Raw silk consists of two filaments that are held together by seracin (silk glue). The silk is degummed (the seracin is removed) and the resulting single filaments are used to manufacture the fiber. The denier per filament (dpf) of individual silk fibers will range from about 0.8 to about 2.0. For fiber manufacture it is common to used silk with a dpf of from about 0.8 to about 1.6 and more preferably a dpf of from about 0.8 to about 1.4. The best grades of silk are easily obtainable from suppliers in China and Japan.

Polyesters are also well known commercially available synthetic polymers that may be used to make the shell or fibrous scaffolding. The most preferred polyester for making this device is polyethylene terephthalate. Generally, polyethylene terephthalate polymers used to make fibers will have a weight average molecular weight of greater than 30,000 preferably greater than 40,000 and most preferably in the range of from about 42,000 to about 45,000. The filaments formed from these polymers should have a tenacity of greater than 5 grams/denier and preferably greater than 7 grams/denier. Polyethylene terephthalate yarns are commonly available from a variety of commercial fiber suppliers (such as E.I. DuPont and Hoechst Celanese). Preferred are commercially available fibers that may be purchased from Hoechst Celanese under the trademark TREVIRA® High Tenacity type 712 and 787 polyester yarns.

A variety of fluoropolymers may also be used to make the shell and the fibrous scaffolding such as polytetrafluoroethylene and polyvinylidene fluoride (i.e. as in U.S. Pat. No. 4,052,550), copolymers and blends thereof. Currently the preferred are the fluoro polymers blends of polyvinylidene fluoride homopolymer and polyvinylidene fluoride and hexafluoropropylene copolymer which is described in U.S. Pat. No. 4,564,013 hereby incorporated by reference herein.

As previously stated the term polypropylene for the purposes of this application include atactic but will be preferably isotactic and syndiotactic polypropylene (such as is described in U.S. Pat. No. 5,269,807 hereby incorporated by reference herein) and blends thereof, as well as, blends composed predominantly of isotactic or syndiotactic polypropylene blended with heterotactic polypropylene and polyethylene (such as is described in U.S. Pat. No. 4,557,264 issued Dec. 10, 1985 assigned to Ethicon, Inc. hereby incorporated by reference) and copolymers composed predominantly of propylene and other alpha-olefins such as ethylene (which is described in U.S. Pat. No. 4,520,822 issued Jun. 4, 1985 assigned to Ethicon, hereby incorporated by reference). The preferred polypropylene material for making fibers is isotactic polypropylene without any other polymers blended or monomers copolymerized therein. The preferred method for preparing the flexible polypropylene fibers of the present invention utilizes as the raw material pellets of isotactic polypropylene homopolymer having a weight average molecular weight of from about 260,00 to about 420,000. Polypropylene of the desired grade is commercially available in both powder and pellet form.

A variety of bioabsorbable polymers can be used to make the shell or fibrous scaffolding of the present invention. Examples of suitable biocompatible, bioabsorbable polymers include but are not limited to polymers selected from the group consisting of aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-, L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, delta-valerolactone, beta-butyrolactone, gamma-butyrolactone, $\epsilon$-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, 2,5-diketomorpholine, pivalolactone, gamma, gamma-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly(iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251–272 (1997). Copoly(ether-esters), for the purpose of this invention, are understood to include those copolyester-ethers as described in the Journal of Biomaterials Research, Vol. 22, pages 993–1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399 hereby incorporated by reference herein. Polyphosphazenes, co-, ter- and higher order mixed monomer-based polymers made from L-lactide, D, L-lactide, lactic acid, glycolide, glycolic acid, para-dioxanone, trimethylene carbonate and epsilon-caprolactone such as are described by Allcock in *The Encyclopedia of Polymer Science*, Vol. 13, pages 31–41, Wiley Intersciences, John Wiley & Sons, 1988 and by Vandorpe, et al in the *Handbook of Biodegradable Polymers*, edited by Domb, et al, Hardwood Academic Press, pp. 161–182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150 hereby incorporated herein by reference. Polyorthoesters such as those described by Heller in *Handbook of Biodegradable Polymers*, edited by Domb, et al, Hardwood Academic Press, pp. 99–118 (1997).

As used herein, the term "glycolide" is understood to include polyglycolic acid. Further, the term "lactide" is understood to include L-lactide, D-lactide, blends thereof, and lactic acid polymers and copolymers.

Particularly well suited for use in the present invention are biocompatible absorbable polymers selected from the group consisting of aliphatic polyesters, copolymers and blends which include but are not limited to homopolymers and copolymers of lactide (which includes D-, L-, lactic acid and D-, L- and meso lactide), glycolide (including glycolic acid), epsilon-caprolactone, p-dioxanone (1,4-dioxan-2-one which is described in U.S. Pat. No. 4,052,988 incorporated herein by reference herein), alkyl substituted derivatives of p-dioxanone (i.e. 6,6-dimethyl-1,4-dioxan-2-one which is described in U.S. Pat. No. 5,703,200 assigned to Ethicon and hereby incorporated by reference), trimethylene carbonate (1,3-dioxan-2-one), alkyl substituted derivatives of 1,3-dioxanone (which are described in U.S. Pat. No. 5,412,068 incorporated herein by reference), delta-valerolactone, beta-butyrolactone, gamma-butyrolactone, epsilon-decalactone, hydroxybutyrate, hydroxyvalerate, 1,4-dioxepan-2-one (described in U.S. Pat. No. 4,052,988 and its dimer 1,5,8,12-tetraoxacyclotetradecane-7,14-dione which is described in U.S. Pat. No. 5,442,032 assigned to Ethicon and hereby incorporated herein by reference), 1,5-dioxepan-2-one, and polymer blends thereof. Preferred fiber materials include but are not limited to copolymers of trimethylene carbonate, epsilon-caprolactone and glycolide (such as are described in U.S. Pat. Nos. 5,431,679 and 5,854,383 hereby herein incorporated by reference) and copolymers of p-dioxanone, trimethylene carbonate and glycolide and copolymers of lactide and p-dioxanone. Preferred are fibers made from lactide and glycolide sometimes referred to herein as simply homopolymers and copolymers of lactide and glycolide and copolymers of glycolide and epsilon-caprolactone i.e. as described in U.S. Pat. Nos. 5,133,739; 4,700,704 and 4,605,730 incorporated herein by reference), most preferred for use as a fiber is a copolymer that is from about 80 weight percent to about 100 weight percent glycolide with the remainder being lactide. More preferred are copolymers of from about 85 to about 95 weight percent glycolide with the remainder being lactide.

The molecular weight of the polymers used in the present invention can be varied as is well know in the art to provide the desired performance characteristics. However, it is preferred to have aliphatic polyesters having a molecular weight that provides an inherent viscosity between about 0.5 to about 5.0 deciliters per gram (dl/g) as measured in a 0.1 g/dl solution of hexafluoroisopropanol at 25° C., and preferably between about 0.7 and 3.5 deciliters per gram (dl/g).

As mentioned above, the outer surface 8 of shell 4 will be perforated with pores 6, which provide a passageway for the ingress and egress of cells to the interior lumen 10 of the immune modulation device 2. At the time of implantation the shell 2, is substantially impermeable to diffusion of water through the non-perforated walls of the shell. The shell 2 is preferably made from one or more absorbable polymers that may become more permeable to aqueous media as they degrade. Absorbable polymers can either be of natural or synthetic origin. The absorbable polymers for the membrane most preferably have a glass transition temperature below physiologic temperature and would therefore be less irritating when implanted in soft tissues. Preferred polymers for the shell would include copolymers with a significant content (at least 30 weight percent) of epsilon-caprolactone or para-dioxanone. A particularly desirable composition includes an elastomeric copolymer of from about 35 to about 45 weight percent epsilon-caprolactone and from about 55 to about 65 weight percent glycolide, lactide (or lactic acid) and mixtures thereof. Another particularly desirable composition includes para-dioxanone homopolymer or copolymers containing from about 0 to about 80 weight percent para-dioxanone and from about 0 to about 20 weight percent of either lactide, glycolide and combinations thereof. The degradation time for the membrane in-vivo is preferably longer than 1 month but is shorter than 6 months and more preferably is longer than 1 month but less than 4 months.

The shell 4 can be of any shape into which the fibrous scaffolding can be placed. The shell can initially have openings that may be later sealed following placement of the fibrous scaffolding 12. The shell 4 can be made by conventional polymer processing techniques including molding, welding, casting, extrusion, injection molding, machining process or combinations thereof. These conventional procedures are well known in the art and described in the Encyclopedia of Polymer Science and Engineering, incorporated herein as reference. Melt extrusion is the preferred method of process as it is rapid, inexpensive, scalable, and can be performed solvent-free for many polymers of interest. Processing aides and plasticizers can be added to the polymer to decrease the processing temperature and/or modify the physical properties of the construct. Processing aides, such as solvents, can be added to decrease the processing temperature by decreasing the glass transition temperature of the polymer. Subsequently, the aide can be removed by either heat and/or vacuum or by passing the extruded construct through a secondary solvent in which the polymer has minimal solubility but is miscible with the processing aide. For example halogenated solvents such as methylene chloride or chloroform can be added to homo- and copolymers of lactide and epsilon-caprolactone. After extrusion, the solvent can be removed through evaporation, vacuum, and/or heat. These solvents could also be extracted by passing the extrudate through a secondary solvent such as alcohol, which has miscibility with the halogenated solvent. Plasticizers can also be incorporated into a polymer to increase its workability, flexibility, or distensibility. Typically these materials work by increasing the free volume of the polymer. For example many citrates, malates and caprilates will work to plasticize many aliphatic polyesters. Oligomers of a given polymer or copolymer can also be used to plasticize a system.

Figure 3:
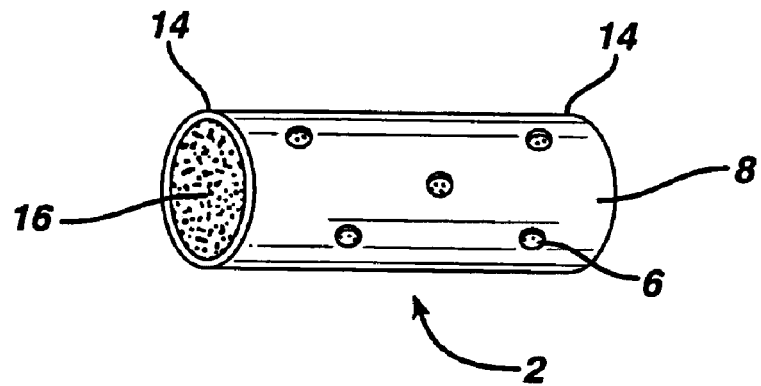
FIG. 3 is a perspective drawing of one embodiment of the immune modulating device showing one end of the device being sealed.

The preferred shapes of the shell are those with a minimal diameter in one dimension to facilitate placement using a small gauge needle. A most preferred shape is a cylinder with an outer diameter preferably less than 1 millimeter and most preferably less than 750 microns. This shape and size facilitates implantation of the device using an 18 gauge needle or smaller. For this embodiment it is preferred that the wall thickness is preferably less than 250 microns and most preferably is less than 150 microns. The pores 6 in the shell 4 generally are large enough to provide for the ingress and egress of cells. The pores are preferably larger than about 10 microns but smaller than about 500 microns in cross-sectional diameter and more preferably are from about 100 to about 400 microns in cross-sectional diameter. The density of perforations preferably does not exceed 25% of the outer surface area of the device and more preferably is below 10% of the outer surface area of the shell of the immune modulation device. The pores can be formed using any appropriate drilling technique (e.g. using a hypodermic needle, mechanical or laser) or alternatively by including a solvent or water soluble solid in the wall polymer which later can be leached out by immersing the tube in the solvent to generate the hole. Alternatively, if biocompatible water soluble particles such as sugars, amino acids, polymers such as PVP, proteins such as gelatin, carbohydrates such as hyalyronic acid and certain carboxy methylcelluloses are used, the device can be implanted with the particles present. Upon exposure to body fluids the pore forming particles can leach out or degrade forming pores. Most of the pore must extend completely through the wall of the device and provide a pathway for cells involved in the immune response to ingress into the interior lumen 10 of the device as well as for antigen and cytokines to diffuse out of the interior lumen 10 of the immune modulation device 2. If the immune modulation device 2 has one or more open ends 14 of the immune modulation device can either be sealed with layer 16 or left open, but are preferably left open. One embodiment of an immune modulation device with one sealed end is illustrated in FIG. 3.

Figure 4:
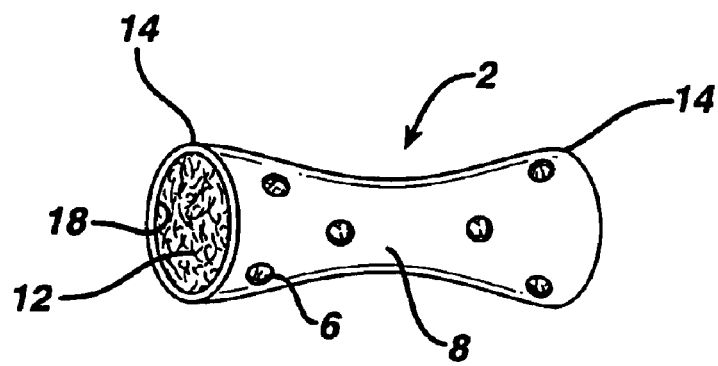
FIG. 4 is a perspective drawing of one embodiment of the immune modulating device showing a device that is crimped.
Figure 5:
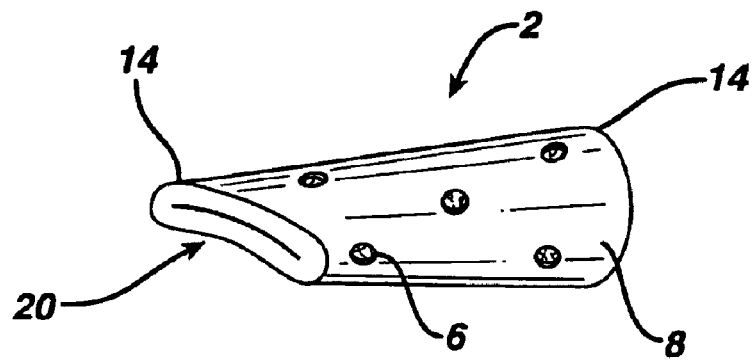
FIG. 5 is a perspective drawing of one embodiment of the immune modulating device showing one end of the device being crimped and sealed.

In another embodiment of the present invention two portions of the interior surface 18 may contact the fibrous scaffolding 12 to restrain movement of the fibers in the immune modulation device 2. For example if the immune modulation device 2 were cylindrical a portion of the device could be crimped about the fibrous scaffolding 12. The crimping could be performed with heating to permanently reshape a portion of the shell 4. One embodiment of a crimped device is illustrated in FIG. 4. Alternatively, the crimping could be performed with cutting and sealing one end of the immune modulation device 2 to form a cylindrical device with one sealed end 20. One embodiment of this device with a sealed end is illustrated in FIG. 5.

Fibers suitable for use in the present device can be made using conventional spinning processes such as melt spinning processes or solution spinning. After spinning the yarns may be quenched, treated with a spin finish, drawn and annealed as is known in the art. The fibrous scaffolding made from these fibers should have a porosity of greater than 20%, more preferably from about 25% to about 95%, and most preferably from about 30% to about 90% to the fibers.

The fibrous scaffold should be made up of filaments having a denier in the range of from about 0.2 to about 10 and preferably a denier from about 0.8 to about 6 and more preferably a denier of from about 1 to about 3. The filaments are commonly extruded in bundles (yarns) having a denier in the range of from about 20 to about 400 denier and preferably about 50 to about 100 denier. The fibers need to be treated to develop the bulk density or porosity need for a fibrous scaffold. The preferred yarns for this application are textured yarns. There are many forms of textured yarns that may be used to form a fibrous scaffolding such as bulked yarns, coil yarns, core bulked yarns, crinkle yarns, entangled yarns, modified stretch yarns, nontorqued yarns, set yarns, stretch yarns and torqued yarns and combinations thereof. Methods for making these yarns are well known and include the false-twisted method, entanglement (e.g. rotoset or air jet entangled), crimping (e.g. gear crimped, edge crimped or stuffer box crimped), and knit-de-knit. Preferably the fibers will be textured by false-twisting method, the stuffer box method or knit-de-knit method of textile texturing. The filaments are texturized to provide a high degree of permanent crimping or random looping or coiling. Crimped fibers are currently preferred. Crimping causes the orientation of the filament to change angle at the crimping points. The angle change is preferably greater than 10 degrees at each crimp point. The crimping can be accomplished through a variety of processes but is most easily generated by feeding the extruded filaments through a stuffer box.

The fibrous scaffolding is preferably a texturized fiber made from an absorbable polymer that can either be of natural or synthetic origin. Each fiber filament preferably has a diameter of less than 20 microns and most preferably less than 15 microns. This imparts to the filaments sufficient flexibility to completely fill the lumen of the tube and provide a suitable surface for cells to colonize in the lumen of the shell. The fibers preferably will take longer than 1 month to biodegrade (via hydrolysis and/or enzymatic activity) in a normal subcutaneous implantation but will completely be biodegraded within 6 months and more preferably between 1 and 4 months. An example of a good polymer for making a fibrous scaffolding is a copolymer of 90% glycolide (or glycolic acid) and 10% lactide (or lactic acid) having an inherent viscosity between about 0.7 to about 1.5 deciliters per gram (dl/g) as measured in a 0.1 g/dl solution of hexafluoroisopropanol at 25° C.

The most significant advantage with the use of fibrous scaffolding is that the fibers can be easily placed within the shell. For example, a textured fiber can be stretched and then the shell extruded, molded or otherwise coated of shaped around them. Following placement of the shell around the stretched fibers, the tension can be relaxed which allows the fibers to assume their crimped shapes and fill the space inside the shell. Unlike sponges that can also be compressed, the textured fibers can be wound onto spools in very long lengths, which can be continuously fed as a core in a core-sheath or wire coating extrusion process. The sheath can be a molten polymer that is co-extruded and drawn with the stretched fibers. Individual units could be created by cutting the core sheath constructs to a desired length. Perforations can be created by piercing the tubing wall to form small holes. Open pore sponges are very difficult to produce in a continuous form and hence would require the shell be formed as small discrete units into which the sponge can be stuffed.

An additional advantage of fibrous scaffolding over sponges in processing is that the spool of fibers will be strong while an open cell sponge will be weak and will tear easily. This is an important consideration in miniaturization of the device. Small bunches of fibers can be stretched, compressed or otherwise exposed to robust mechanical processing. In contrast, small dimension sponges tear or break easily and can only be subjected to gentle processing. Formation of sub-millimeter devices necessarily subjects the filling to significant stresses in order to fit within the small dimensions of the shell. Miniaturization is very important in minimizing patient pain and discomfort following implantation of the device. Hence the use of fibers, which can be compressed more substantially that an open-cell sponge, enables a smaller device which is preferable from the patient's standpoint.

At first glance it may appear desirable to fill the shell with simple straight fibers. However, straight fibers would settle and bunch in the shell over time and would not provide a hospitable environment for ingress of large numbers of cells. Additionally, straight fiber would require that the device be modified to prevent the fibers from fall out of the device during handling. If the fibers were densely packed or braided so as to provide an interference fit in the shell there would not be sufficient porosity for cell colonization. Texturizing the fibers allows them to effectively fill space while maintaining porosities needed for colonization with high cell number densities. This low bulk density property of the texturized fibers enables an interference fit with the walls of the shell without having to worry about compaction of the filling during storage and handling.

The textured fibers can either be filled into a preformed tube or the tube can be extruded around the filaments. During the filling process it may be desirable to stretch the filaments to a straight orientation. This radially compresses the fibers to a much smaller diameter than they occupy when in a relaxed state. The void volume in the lumen of the tube is preferably greater than 30% and more preferably greater than 50%. Once relaxed the textured filaments should completely fill the lumen of the device and should stay in place in the lumen due to the compressive force exerted by the tubing walls on the filling.

A preferred process for generating the textured fiber filled tubes consists of extruding the tubing around the stretched filaments in a continuous manner. This can be accomplished by having the textured fiber wound on a spool and fed under tension through the lumen of an extruder die as a core around which a sheath of wall polymer is continuously extruded. Perforations can later be drilled through the wall of the polymer either mechanically or using electromagnetic radiation (e.g. laser ablation). It is especially desirable to adjust the depth of drilling so that the wall is completely punctured but the filling is not damaged. With electromagnetic radiation this can be accomplished by provided just enough focused energy to ablate through the wall of the tube. Alternatively it is possible to fill a preformed tube by tying the textured fiber to a thin wire or needle and then dragging the textured filaments under tension through the tubing. Additionally, it is possible to fill a preformed tube by using a pressure differential (e.g. vacuum or blown air) to pull the textured filament through the tubing. In this configuration the perforations in the tube can be created either pre or post filling of the lumen. The length of the textured fiber filled tube is cut to be greater than a few millimeters and more preferably greater than 5 millimeters.

The lumen of the device is filled with an antigen, mixture of antigens and optionally one or more cytokines, prior to implantation. The antigen can either be in a dry or wet form. Potential antigens include peptides, proteins, nucleotides, carbohydrates or even cells or cell fragments. The antigen or antigens can be bioavailable at the time of implantation (for immediate release with optionally a portion in a sustained release form) or designed to be bioavailable after implantation (e.g. 3 days after). The antigen or antigens can be supplied in a sustained release form, such as encapsulated in microparticles, can be supplied in a naked form or in combinations thereof. One method by which antigen can be loaded is to suspend it in a suitable liquid which is then injected or pumped into the lumen of the filled tube. The textured fiber filling must be under sufficient compression as to stay in place through the convection of the fluid. The fluid filled device can then be implanted or the filling fluid can be dehydrated or lyophilized prior to implantation leaving behind in the lumen of the filled device the desired antigen or antigens. Alternatively the textured fiber may be impregnated with the antigen etc. prior to insertion into the shell. The dehydrated system will rehydrate following implantation that will present the antigen in a suitable form for generating the desired immunomodulatory response. A particularly convenient site of implantation is subcutaneous insertion directly beneath the skin, however any site which offers access to antigen presenting cells, macrophages and other cells of the immune system is acceptable. Desired immunomodulatory responses can include either generation of humoral and/or cellular immunity against the desired antigen or alternatively desensitization towards particular allergen or cell types.

Any specific antigen or combination of synthetic or natural antigens may be employed as the antigenic substance for incorporation in the immune modulation device and subsequent implantation in the animal. The antigens can be from bacterial, fungal, viral, cellular (e.g. from parasites or in autoimmune treatments from animal tissue) or synthetic sources which contain at least one epitope to which the immune system of the animal will respond. In immunization the antigen is desired to induce protective immunity to the animal to which it is administered. The antigen source can be preparations of killed microorganisms; living weakened microorganisms; inactivated bacterial toxins (toxoids); purified macromolecules; recombinantly produced macromolecules and the like. Preferably for mammals, the antigen or mixtures of antigens will be derived from bacterial or viral sources with polyvalent antigenic domains being present. Suitable bacterial antigen sources include, but are not limited to, *Actinobacillus equuli, Actinobacillus lignieresi, Actinobaccilus seminis, Aerobacter aerogenes, Borrelia burgdorferi, Borrelia garinii, Borrelia afzelii, Babesia microti, Klebsiella pneumoniae, Bacillus cereus, Bacillus anthracis, Bordetella pertussis, Brucella abortus, Brucella melitensis, Brucella ovis, Brucella suis, Brucella canis, Campylobacter fetus, Campylobacter fetus intestinalis, Chlamydia psittaci, Chlamydia trachomatis, Clostridium tetani, Corynebacterium acne* Types 1 and 2, *Corynebacterium diphtheriae, Corynebacterium equi, Corynebacterium pyogenes, Corynebacterium renale, Coxiella burnetii, Diplococcus pneumoniae, Escherichia coli, Ehrlichia phagocytophila, Ehrlichia equi, Francisella tularensis, Fusobacterium necrophorum, Giardia lambia, Granuloma inguinale, Haemophilus influenzae, Haemophilus vaginalis*, Group b *Hemophilus ducreyi, Lymphopathia venereum, Leptospira pomona, Listeria monocytogenes, Microplasma hominis, Moraxella bovis, Mycobacterium tuberculosis, Mycobacterium laprae, Mycoplasma bovigenitalium, Neisseria gonorrhea, Neisseria meningitidis, Pseudomonas maltophiia, Pasteurella multocida, Pasteurella hamemolytica, Proteus vulgaris, Pseudomonas aeruginosa, Plasmodium berghei, Plasmodium falciparum, Plasmodium*

*malariae, Plasmodium ovale, Plasmodium vivax, Rickettsia prowazekii, Rickettsia mooseri, Rickettsia rickettsii, Rickettsia tsutsugamushi, Rickettsia akari, Salmonella abortus ovis, Salmonella abortus equi, Salmonella dublin, Salmonella enteritidis, Salmonella heidleberg, Salmonella paratyphi, Salmonella typhimurium, Shigella dysenteriae, Staphylococcus aureus, Streptococcus ecoli, Staphylococcus epidermidis, Streptococcus pyrogenes, Streptococcus mutans, Streptococcus Group B, Streptococcus bovis, Streptococcus dysgalactiae, Streptococcus equisimili, Streptococcus uberis, Streptococcus viridans, Treponema pallidum, Vibrio cholerae, Yersina pesti, Yersinia enterocolitica* and combinations thereof. Suitable fungi antigen sources including, but are not limited to, *Aspergillus fumigatus, Blastomyces dermatitidis, Candida albicans, Crytococcus neoformans, Coccidioides immitis, Histoplasma capsulatum* and combinations thereof. Suitable viral antigen sources from viral sources include, but are not limited to, influenza, HIV, hanta virus (e.g. Sin Nombre virus), Mumps virus, Rubella virus, Measles virus, Smallpox virus, Hepatitis virus, (e.g. A, B, C, D, E), Rift Valley Fever (i.e. Plebovirus), viral encephalitis, (e.g. Eastern equine encephalitic virus, St. Louis encephalitic virus, Western equine encephalitic virus, West Nile Virus), human papilloma virus, cytomegalovirus, polio virus, rabies virus, Equine herpes virus, Equine arteritis virus, IBR—IBP virus, BVD—MD virus, Herpes virus (humonis types 1 and 2) and combinations thereof. Suitable parasite antigen sources include, but are not limited to, *Schistosoma, Onchocerca*, parasitic amoebas and combinations thereof. Preferred infectious diseases that this device and method may provide prophylaxis against include viruses such as influenza, HIV, human papilloma, hepatitis, cytomegalovirus, polio and rabies; bacteria for example *E. coli, Pseudomonas, Shigella, Treponema pallidum, Mycobacterium* (*tuberculosis* and *laprae*), *Chlamydia, Rickettsiae*, and *Neisseria*; fungi such as *Aspergillus* and *Candida*; and parasitic multicellular pathogens.

Suppression of the immune response may also be desirable to treat conditions, such as allergies, or to prepare patients for the exposure to foreign antigens, such as for transplant. Inappropriate immune responses are believed to be the underlying etiology in a number of autoimmune and other diseases, such as type I diabetes, rheumatoid arthritis, multiple sclerosis, uveitis, systemic lupus erythematosus, myasthenia gravis, and Graves' disease. By implanting in an individual a device of the present invention containing the suspect antigen, entry of cells primed to recognize the antigen can be induced to undergo apoptosis, and be eliminated from the immune system. Elimination of progenitor antigen-specific cells can permit the later transplant of foreign antigens without rejection.

Further utilities of the present invention include improvements in the generation of polyclonal antibodies (immune serum) and nonclonal antibodies in laboratory animals and obtaining the desired isotype of antibody so generated. In one embodiment, a procedure for preparing polyclonal (immune serum) and monoclonal antibodies against an antigen available only in minute quantities can be performed by the device of the present invention. The device can be provided with a small amount of the rare antigen, in order to immunize the animal, after which spleen cells can be harvested. This procedure offers an improvement over current tedious and unpredictable method of introducing the rare antigen directly into the spleen. Furthermore, the need for a boost immunization may be obviated by use of the device of the present invention, and, in addition, an immune response will be generated more quickly. A shortened time required to immunize animals will allow the generation of monoclonal antibodes more rapidly. In another embodiment, immune cells for the production of hybridomas can be harvested from the device after immunization of an animal with an antigen provided within the device. This procedure can also be used to generate human monoclonal antibodies, by implanting a device of the present invention into an individual, loading the device with antigen, and then harvesting immune cells from the device for the production of hybridomas. The above-mentioned polyclonal antibodies (immune serum) and monoclonal antibodies can be used for diagnosis, basic research, imaging and/or therapy. In another embodiment, human monoclonal antibodies can be generated using the device of the present invention implanted in a severe combined immunodeficiency (SCID) mouse, by the following procedure. First, human peripheral blood lymphocytes are injected into a SCID mouse, wherein the human lymphocytes populate the murine immune system. After implantation of a device of the present invention comprising the desired antigen which is bioavailable after implantation, subsequent harvesting of cells from the device will provide human B lymphocytes cells which can then be used to prepare hybridomas which secrete human antibodies against the desired antigen.

A further utility of the device of the present invention is in collection of immune cells from a mammal for later reintroduction into the mammal. Cells can be removed from the device, for example, by aspiration from the implanted device or collection from the device after removal from the body by dissolving the polymer matrix, subsequent storage of the cells, for example by cryopreservation, and reintroduction into the mammal at a later time. This can be particularly useful for mammals undergoing whole body radiation therapy. A device of the present invention, without containing antigen, can be implanted and maintained for a time sufficient to allow immune cells to migrate into the device (e.g. seven to ten days). Subsequently the device or its contents are removed and the cells contained therein cryopreserved. Following radiation therapy, the mammal can have the cells reintroduced into the body, whereby the cells will reconstitute the immune system. In another embodiment of this utility, co-stimulatory factors such as cytokines which induce the proliferation of immune cells can be introduced into the device to increase the yield of cells within the device, before harvesting. In a further embodiment, immune cells collected from a device provided with antigen can be used for active immunization, wherein the cells can be stored and then reintroduced into the mammal after, for example, a course of chemotherapy or other therapeutic manipulation. In a still further embodiment, cells collected from a device can be cyropreserved, and at a later time be exposed to the antigen (for example, a cancer antigen) for ex-vivo propagation of T cells prior to introduction into the body, for adoptive immunotherapy.

EXAMPLES

The following examples illustrate the construction of a textured fiber filled device for generating an immunomodulatory response. Those skilled in the art will realize that these specific examples do not limit the scope of this invention and many alternative forms of an antigen loaded textured fiber filled device could also be generated within the scope of this invention.

Example 1
Textured Fibrous Filling

Figure 2:
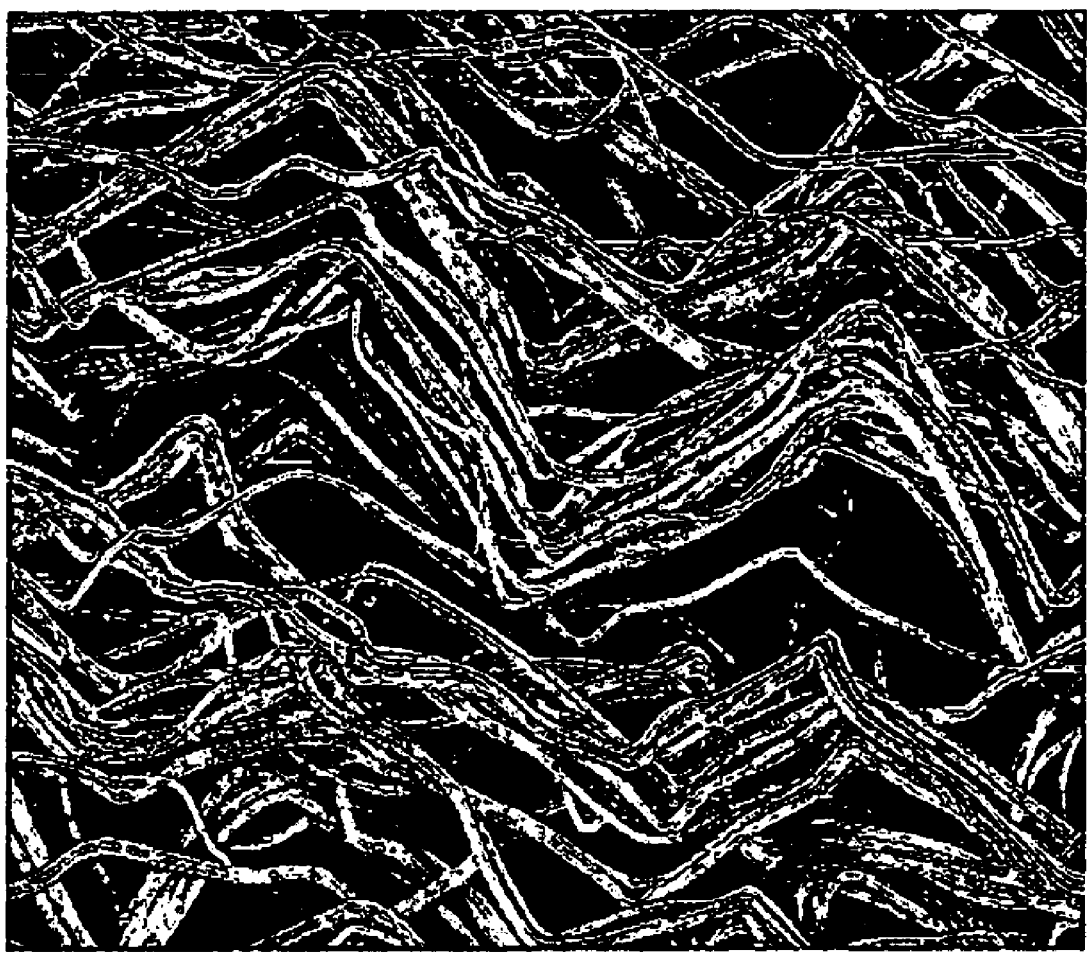
FIG. 2 is a scanning electron micrograph of one embodiment of a textured fiber suitable for use in the present invention made by the process described in Example 1.

Fiber texturing was performed using a Techtex® HDC10 texturizer (Techniservice, 738 West Cypress Street, Kennett Square, Pa. 19348-0817). Nine spools of 56 denier natural 90/10 glycolide-co-lactide (IV of about 1.1 deciliters per gram (dl/g) as measured in a 0.1 g/dl solution of hexafluoroisopropanol at 25° C. The filaments had been drawn about 5× (original length compared to final length). The filaments were placed on the creel and combined into a single 504 denier tow by running the drawn yarns together through a common eyelet. The individual yarn filament diameters were between 12–20 μm. A pretension of 5–7 grams was used for each yarn by passing them through the gate tensioner. The large yarn tow was then passed over a heated godet with the separator roller (15 wraps) with the heated godet being set to a temperature of 130° C. This yarn tow was then fed into the stuffer box by two crimper rolls. The clearance between the stuffer box and rollers was 0.012 inches and the temperature in the stuffer box was about 50° C. (the box was not heated, the elevated temperature of 50° C. came from the yarn, heated on the godet). Uniformity of crimp texture is maintained through accurate control of the crimped column height in the stuffer box. The column height control is provided by the optical sensor located in the stuffer box and signaling the take up winder inverter to speed up/slow down. The stuffer box optical sensor was set to hole no. 8 from the top of the box. After the stuffer box, the textured yarn tow passed through the gate tensioner set at 5 grams for combining and keeping all yarns in the tow under the same tension. The crimped yarn then passed the overfeed rolls to reduce high yarn tension prior to winding on the take up winder. The take up winder speed was set at 170 m/min. An image of the resulting textured fiber is shown in FIG. 2.

Example 2
Membrane Formation

Membranes were formed from both poly(para-dioxanone) (PDO) and a copolymer of 35/65 epsilon-caprolactone/glycolide (CAP/GLY). The inherent viscosity (dl/g) of the PDO and CAP/GLY, as measured in a 0.1 g/dl solution of hexafluoroisopropanol (HFIP) 25° C., were 1.80 and 1.30, respectively. All membranes were formed by extrusion using a ¾-inch Brabender single-screw extruder (C.W. Brabender® Instruments, Inc., So. Hackensack, N.J.) under flowing nitrogen. Membranes with several inner and outer dimensions were formed. Extrusion conditions for the extruded membranes are shown in Table 1. Immediately following exit from the die, all membranes were run through a 12-foot cooling trough filled with chilled water at a temperature of 5–10° C. For the CAP/GLY membranes, short segments (~2–3 ft.) were cut and hung from one end at room temperature to allow solidification and crystallization of the polymer.

TABLE 1

Extrusion conditions

| Polymer | Die size Die × tip (mil) | $T_{zone1}$ (° C.) | $T_{zone2}$ (° C.) | $T_{zone3}$ (° C.) | $T_{adapt.}$ (° C.) | $T_{die}$ (° C.) | $P_{block}$ (psi) | $P_{air}$ (psi) | Screw speed (rpm) | Take-off (FTM) | OD (mm) | ID (mm) |
|---|---|---|---|---|---|---|---|---|---|---|---|---|
| 35/65 CAP/GLY | 170 × 138 | 140 | 145 | 145 | 145 | 140 | 1900 | 0.1 | 12 | 20 | 2.0 | 1.5 |
| 35/65 CAP/GLY | 102 × 83 | 140 | 145 | 145 | 145 | 145 | 4480 | 0 | 4 | 18 | 1.03 | 0.83 |
| 35/65 CAP/GLY | 53 × 40 | 140 | 145 | 145 | 145 | 140 | 4300 | 0.1 | 3 | 14 | 0.9 | 0.7 |
| 35/65 CAP/GLY | 56 × 40 | 140 | 145 | 150 | 150 | 150 | 2470 | 0.3 | 4 | 34 | 0.65 | 0.45 |
| PDO | 102 × 83 | 130 | 135 | 135 | 135 | 135 | 5000 | 0 | 5 | 20 | 1.03 | 0.83 |
| PDO | 102 × 83 | 145 | 150 | 150 | 150 | 150 | 3750 | 0 | 5 | 20 | 0.65 | 0.45 |

After extrusion, the membranes were cut to the desired length (2–2.5 cm) using a razor blade. Membrane perforations were formed at Resonetics, Inc. (Nashua, N.H.) using an excimer laser (Lambda-Physik EMG201MSC Excimer Laser) operating at a wavelength of 193 nm. The laser was coupled to a Resonetics engineering workstation consisting of a mask projection imaging beam delivery system and a three-axis (XYtheta) computerized motion control system. Hole sizes ranging between 100 and 500 microns were formed through the membrane walls. Drilling parameters for the different tubing are shown in Table 2.

TABLE 2

Laser drilling conditions

| Polymer | OD/ID (mm/mm) | Fluence (J/cm$^2$) | Pulse rate (Hz) | ~Etch rate (μm/pulse) |
|---|---|---|---|---|
| 35/65 CAP/GLY | 2.0 × 1.5., 0.9 × 0.7 | 10 | 50 | 0.63 |
| 35/65 CAP/GLY | 2.0 × 1.5 | 3.5 | 50 | 0.56 |
| 35/65 CAP/GLY | 2.0 × 1.5 | 0.7 | 10 | 0.5 |
| 35/65 CAP/GLY | 1.03 × 0.83, 0.65 × 0.45 | 2 | 25 | 0.67 |
| PDO | 1.03 × 0.83, 0.65 × 0.45 | 2.6 | 50 | 0.5 |

Example 3
VLN Construct Formation

The textured fiber filling from Example 1 was placed inside the membranes discussed in Example 2 as follows. Textured fiber was attached to a small needle or thin filament of wire and pulled through the membrane. The fiber was cut to the length of the membrane. Available porosity was calculated from the volume of the inner lumen of the membrane, weight of textured yarn placed inside of the membrane, and the density of the fibers used. Table 3 shows several of the construct geometries and resultant porosities.

TABLE 3

*Absorbable VLN constructs containing textured fiber.*

| Membrane Composition | OD/ID/length (mm/mm/mm) | Hole diameter (μm) | # holes | Fiber weight (mg) | ~Percent porosity | Sample # |
|---|---|---|---|---|---|---|
| CAP/GLY | 2.0/1.5/25 | 300 | 20 | 12 | 80% | 1 |
| CAP/GLY | 2.0/1.5/20 | 300 | 16 | 10 | 80% | 2 |
| CAP/GLY | 2.0/1.5/20 | 300 | 12 | 10 | 80% | 3 |
| CAP/GLY | 2.0/1.5/20 | 300 | 8 | 10 | 80% | 4 |
| CAP/GLY | 2.0/1.5/20 | 300 | 4 | 10 | 80% | 5 |
| CAP/GLY | 2.0/1.5/20 | not applicable | 0 | 10 | 80% | 6 |
| CAP/GLY | 2.0/1.5/25 | 300 | 16 | 10 | 83% | 7 |
| CAP/GLY | 2.0/1.5/25 | 300 | 16 | 15 | 75% | 8 |
| CAP/GLY | 2.0/1.5/20 | 300 | 20 | 8 | 83% | 9 |
| CAP/GLY | 2.0/1.5/20 | 300 | 20 | 12 | 75% | 10 |
| CAP/GLY | 0.65/0.45/25 | 150 | 4 | 2 | 65% | 11 |
| CAP/GLY | 0.65/0.45/25 | 150 | 12 | 2 | 65% | 12 |
| CAP/GLY | 0.65/0.45/25 | 150 | 20 | 2 | 65% | 13 |
| PDO | 0.65/0.45/25 | 150 | 4 | 1.3 | 75% | 14 |
| PDO | 0.65/0.45/25 | 150 | 8 | 1.3 | 75% | 15 |
| PDO | 0.65/0.45/25 | 150 | 12 | 1.1 | 80% | 16 |
| PDO | 0.65/0.45/25 | 150 | 16 | 1.3 | 75% | 17 |

Example 4

Prior art (WO 99/44583) has demonstrated that a nonabsorbable device using a 25 mm length of silicone tubing with an internal diameter of 1.5 mm and outer diameter of 2 mm, fitted with a 25 mm-long segment of hydroxylated polyvinyl acetate sponge induces a more robust immune response to the influenza vaccine (in BALB/c mice) than traditional intramuscular injections with and without the use of traditional adjuvants such as Ribi. Similarly the device of the present invention such as the absorbable, fiber-filled device described in Example 3 (Sample #1) could be loaded with ~100 ng of influenza antigen (FLUSHIELD® influenza virus vaccine, trivalent, Types A & B; obtained from Henry Schein®, Melville N.Y.). Female BALB/c mice (6–8 weeks old) would be anesthetized with Avertin. One device per animal could be inserted through a 0.5-cm dorsal midline incision on day 1.

At appropriate intervals post-immunization the mice could be bled and the sera tested for influenza-specific humoral response, using conventional ELISA or other appropriate protocols to determine immune response. The optimum dosage of antigen of the device could be determined by developing dose response curves at appropriate time intervals post implantation. Similarly, the cell population in the device could be determined at appropriate intervals (e.g. days 3, 7, 10 etc.) to verify the migration of cells into the device, cell types in the device and optimum configuration of holes etc. to provide the most advantageous conditions for immune modulation in any animal with a particular antigen (or antigens).

We claim:

1. An immune modulation device that is suitable for use in modulating an immune response in animals, comprising:
an impermeable biocompatible shell having an outer surface comprising a plurality of pores of suitable size to allow the ingress and egress of immune cells, said impermeable biocompatible shell having an interior lumen,
a biocompatible fibrous scaffolding being disposed within said interior lumen, said fibrous scaffolding comprising textured yarn containing crimped fibers having crimp points, wherein the orientation of filaments in said crimped fiber changes angle at said crimp points; and
an antigen disposed within said interior lumen.

2. The immune modulation device of claim 1 wherein the fibrous scaffolding has a porosity of from about 25 percent to about 95 percent.

3. The immune modulation device of claim 1 wherein the fibrous scaffolding is made from filaments with a diameter of less than 20 microns.

4. The immune modulation device of claim 1 wherein the fibrous scaffolding is made from filaments with a denier of from about 0.2 to about 10.

5. The immune modulation device of claim 1 wherein the fibrous scaffolding is made from filaments with a denier of from about 0.8 to about 6.

6. The immune modulation device of claim 1 wherein the fibrous scaffolding is made from a bundle of filaments having a total denier of from about 20 to about 400 denier.

7. The immune modulation device of claim 1 wherein the textured yarn is selected from the group consisting of bulked yarns, coil yarns, core bulked yarns, crinkle yarns, entangled yarns, modified stretch yarns, nontorqued yarns, set yarns, stretch yarns, torqued yarns, and combinations thereof.

8. The immune modulation device of claim 1 wherein the immune modulation device has a three dimensional shape selected from the group consisting of spherical, cylindrical, rectangular, and rhomboidal.

9. The immune modulation device of claim 7 wherein the immune modulation device is cylindrical in shape.

10. The immune modulation device of claim 9 wherein the cylindrically shaped immune modulation device has an outer diameter of less than 1 millimeter.

11. The immune modulation device of claim 10 wherein the cylindrically shaped immune modulation device has an outer diameter of less than 750 microns.

12. The immune modulation device of claim 9 wherein the cylindrically shaped immune modulation device has a wall thickness of less than 250 microns.

13. The immune modulation device of claim 12 wherein the cylindrically shaped immune modulation device has a wall thickness of less than 150 microns.

14. The immune modulation device of claim 1 wherein the pores on the outer surface of the immune modulation device comprise less than 25 percent of the outer surface.

15. The immune modulation device of claim 14 wherein the pores range in size from about 10 to about 500 microns.

16. The immune modulation device of claim 1 wherein the immune modulation device is bioabsorbable.

17. The immune modulation device of claim 16 wherein each of the biocompatible shell and the biocompatible scaffolding are independently made from a polymer selected from the group consisting of aliphatic polyesters, poly (amino acids), copoly(ether-esters), polyalkylenes oxalates, polyamides, tyrosine derived polycarbonates, poly (iminocarbonates), polyorthoesters, polyoxaester, polyamidoesters, polyoxaesters containing amine groups, poly(anhydrides), polyphosphazenes, biomolecules; and blends thereof.

18. The immune modulation device of claim 17 wherein both the biocompatible shell and the biocompatible scaffolding are made from an aliphatic polyester.

19. The immune modulation device of claim 18 wherein the aliphatic polyester is selected from the group consisting of homopolymers and copolymers of lactide, glycolide, ε-caprolactone, p-dioxanone, trimethylene carbonate, alkyl derivatives of trimethylene carbonate, delta-valerolactone, beta-butyrolactone, gamma-butyrolactone, ε-decalactone, hydroxybutyrate, hydroxyvalerate, 1,4-dioxepan-2-one, 1,5-dioxepan-2-one, 6,6-dimethyl-1,4-dioxan-2-one, 2,5-diketomorpholine, pivalolactone, gamma, gamma-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one, and polymer blends thereof.

20. The immune modulation device of claim 19 wherein the shell is made from an aliphatic polyester selected from the group consisting of homopolymers and copolymers of lactide, glycolide, ε-caprolactone, p-dioxanone, trimethylene carbonate, alkyl derivatives of trimethylene carbonate, 1,4-dioxepan-2-one, 1,5-dioxepan-2-one, 6,6-dimethyl-1,4-dioxan-2-one, and polymer blends thereof.

21. The immune modulation device of claim 19 wherein the shell is made from an aliphatic polyester selected from the group consisting of poly(p-dioxanone), glycolide-co-ε-caprolactone, glycolide-co-trimethylene carbonate, glycolide-co-1,5-dioxepan-2-one, 6,6-dimethyl-1,4-dioxan-2-one, and blends thereof.

22. The immune modulation device of claim 1 wherein the biocompatible fibrous scaffolding is made from an aliphatic polyester selected from the group consisting of homopolymers and copolymers of lactide, glycolide, ε-caprolactone, p-dioxanone, trimethylene carbonate, alkyl derivatives of trimethylene carbonate, 1,4-dioxepan-2-one, 1,5-dioxepan-2-one, 6,6-dimethyl-1,4-dioxan-2-one, and polymer blends thereof.

23. The immune modulation device of claim 22 wherein the biocompatible fibrous scaffolding is made from an aliphatic polyester selected from the group consisting of polyglycolide, poly(p-dioxanone), glycolide-co-ε-caprolactone, glycolide-co-trimethylene carbonate, and glycolide-co-lactide.

24. The immune modulation device of claim 1 wherein the shell is made from poly(p-dioxanone) and the fibrous scaffolding is made from a copolymer of about 90 weight percent glycolide and about 10 weight percent lactide.

25. The immune modulation device of claim 1 wherein the shell is made from a copolymer of from about 35 to about 45 weight percent epsilon-caprolactone and from about 55 to about 65 weight percent glycolide and the fibrous scaffolding is made from a copolymer of about 90 weight percent glycolide and about 10 weight percent lactide.

26. The immune modulation device of claim 1 wherein the antigen is selected from the group of natural antigens, synthetic antigens and combinations thereof.

27. The immune modulation device of claim 26 wherein the natural antigen is derived from a microbe selected from the group consisting of *Actinobacillus equuli, Actinobacillus lignieresi, Actinobaccilus seminis, Aerobacter aerogenes, Borrelia burgdorferi, Borrelia garinii, Borrelia afzelii, Babesia microti, Klebsiella pneumoniae, Bacillus cereus, Bacillus anthracis, Bordetella pertussis, Brucella abortus, Brucella melitensis, Brucella ovis, Brucella suis, Brucella canis, Campylobacter fetus, Campylobacter fetus intestinalis, Chlamydia psittaci, Chlamydia trachomatis, Clostridium tetani, Corynebacterium acne* Types 1 and 2, *Corynebacterium diphtheriae, Corynebacterium equi, Corynebacterium pyogenes, Corynebacterium renale, Coxiella burnetii, Diplococcus pneumoniae, Escherichia coli, Ehrlichia phagocytophila, Ehrlichia equi, Francisella tularensis, Fusobacterium necrophorum, Giardia lambia, Granuloma inguinale, Haemophilus influenzae, Haemophilus vaginalis,* Group b *Hemophilus ducreyi, Lymphopathia venereum, Leptospira pomona, Listeria monocytogenes, Microplasma hominis, Moraxella bovis, Mycobacterium tuberculosis, Mycobacterium laprae, Mycoplasma bovigenitalium, Neisseria gonorrhea, Neisseria meningitidis, Pseudomonas maltophiia, Pasteurella multocida, Pasteurella hamemolytica, Proteus vulgaris, Pseudomonas aeruginosa, Plasmodium berghei, Plasmodium falciparum, Plasmodium malariae, Plasmodium ovale, Plasmodium vivax, Rickettsia prowazekii, Rickettsia mooseri, Rickettsia rickettsii, Rickettsia isutsugamushi, Rickettsia akari, Salmonella abortus ovis, Salmonella abortus equi, Salmonella dublin, Salmonella enteritidis, Salmonella heidleberg, Salmonella paratyphi, Salmonella typhimurium, Shigella dysenteriae, Staphylococcus aureus, Streptococcus ecoli, Staphylococcus epidermidis, Streptococcus pyrogenes, Streptococcus mutans, Streptococcus* Group B, *Streptococcus bovis, Streptococcus dysgalactiae, Streptococcus equisimili, Streptococcus uberis, Streptococcus viridans, Treponema pallidum, Vibrio cholerae, Yersina pesti, Yersinia enterocolitica, Aspergillus fumigatus, Blastomyces dermatitidis, Candida albicans Crytococcus neoformans, Coccidioides immitis, Histoplasma capsulatum,* influenza viruses, HIV, hanta viruses, human papilloma virus, cytomegalovirus, polio virus, rabies virus, Equine herpes virus, Equine arteritis virus, IBR—IBP virus, BVD—MD virus, Herpes virus (humonis types 1 and 2), Mumps virus, Rubella virus, Measles virus, Smallpox virus, Hepatitis viruses, Rift Valley Fever virus, viral encephalitises, *Schistosoma, Onchocerca,* parasitic amoebas, and combination thereof.

28. The immune modulation device of claim 1 wherein the impermeable biocompatible shell having an outer surface and an interior lumen is formed by extruding a biocompatible polymer.

29. The immune modulation device of claim 9 wherein the cylinder has a first end and a second end, said first end being sealed.

30. The immune modulation device of claim 1 wherein said orientation of said crimped filaments at said crimp points changes angle by at least 10 degrees.

31. The immune modulation device of claim 1 comprising at least one opening other than said pores through which said fibers may pass.

32. The immune modulation device of claim 9 wherein the cylinder has a first end and a second end, wherein at least one of said first and second ends is open.

* * * * *